(12) United States Patent
Yuan et al.

(10) Patent No.: US 7,879,353 B2
(45) Date of Patent: Feb. 1, 2011

(54) CONTROLLED OR SUSTAINED-RELEASE FORMULATION

(75) Inventors: Jenny Yuan, Branchburg, NJ (US); Sasa Andjelic, New York, NY (US)

(73) Assignee: Ethicon, Inc., Somerville, NJ (US)

( * ) Notice: Subject to any disclaimer, the term of this patent is extended or adjusted under 35 U.S.C. 154(b) by 1594 days.

(21) Appl. No.: 11/110,967

(22) Filed: Apr. 20, 2005

(65) Prior Publication Data

US 2006/0240104 A1 Oct. 26, 2006

(51) Int. Cl.
*A61K 9/22* (2006.01)
(52) U.S. Cl. .................. 424/468; 424/423; 424/484
(58) Field of Classification Search .................. 424/423, 424/449, 468, 484
See application file for complete search history.

(56) References Cited

U.S. PATENT DOCUMENTS

| | | | |
|---|---|---|---|
| 3,997,512 A | 12/1976 | Casey et al. | |
| 4,048,256 A | 9/1977 | Casey et al. | |
| 4,076,798 A | 2/1978 | Casey et al. | |
| 4,095,600 A | 6/1978 | Casey et al. | |
| 4,118,470 A | 10/1978 | Casey et al. | |
| 4,122,129 A | 10/1978 | Casey et al. | |
| 4,938,968 A * | 7/1990 | Mehta | 424/495 |

OTHER PUBLICATIONS

Yukinari, et al. "Swelling controlled zero-order and sigmodial drug release from thermo-responsive poly(N-isopropylacrylamide-co-butyl methacrylate) hydrogel" J. Biomater. Sci. Polymer Edn, (1993) vol. 4, No. 5, pp. 545-556.

Okano, et al., "Thermally on-off switching polymers for drug permeation and release" J. of Controlled Release, (1990), vol. 11, pp. 255-265.

* cited by examiner

*Primary Examiner*—Frederick Krass
*Assistant Examiner*—Walter E Webb
(74) *Attorney, Agent, or Firm*—Roberts Mlotkowski Safran & Cole, P.C.

(57) ABSTRACT

A formulation comprising: a co-polyester comprising (a) the reaction product of a polycondensation polyester and (b) glycolide; wherein the polycondensation polyester comprises the reaction product of diglycolic acid and/or a derivative thereof and ethylene glycol, and the co-polyester comprises about 40% by weight of the polycondensation polyester based on the total weight of the co-polyester; and a drug selected from the group consisting of indomethacin, diclofenac sodium, and ketoprofen.

7 Claims, 5 Drawing Sheets

CONTROLLED OR SUSTAINED-RELEASE FORMULATION

FIELD OF THE INVENTION

The present invention relates to a controlled or sustained release formulation and the use of a co-polyester that comprises the reaction product of a polycondensation polymer and at least one lactone as a drug delivery carrier in such controlled or sustained-release formulation.

BACKGROUND OF THE INVENTION

Plasma drug level oscillations are commonly associated with multiple dosing of conventional dosage forms. For example, conventional dosage forms often exhibit a deleterious burst phenomenon where most or nearly all of the drug is released into the plasma in a relatively short period of time. One aspect of research on controlled or sustained-release delivery systems involves designing a system that has the potential to produce steady-state plasma drug levels. Ideally, drug level oscillations should be minimized and more constant plasma drug levels over time should be achieved by the use of controlled or sustained-release formulations.

With many drugs, the basic goal of therapy is to provide a delivery system that is capable of providing steady-state plasma or tissue drug levels that are considered therapeutically effective and to maintain these levels without encountering any safety concerns. A basic objective is to optimize the delivery of drugs to maintain a level of efficacy in spite of fluctuations that may take place in the environment where the drugs are released. Therefore, a controlled or sustained-release formulation should be capable of providing a therapeutically effective level of drug, which allows a practitioner to target the therapeutic window of efficacy of the drug, while controlling the plasma drug levels without the deleterious burst phenomenon commonly associated with conventional drug forms. In certain pharmacological applications where high initial concentration of drug is needed, burst release profile could also be desired.

Additionally, practioners can achieve desirable therapeutic advantages by the use of controlled or sustained-release formulations that are able to minimize the frequency of dosing that is sometimes required for a variety of dosage forms. This allows one to improve patient compliance and make the product more convenient.

"Controlled or sustained-release" as used herein refers to the release of a bioactive compound from a medical device surface at a predetermined rate. Controlled or sustained release implies that the bioactive compound does not come off the medical device surface sporadically in an unpredictable fashion and does not "burst" off of the device upon contact with a biological environment. However, the controlled or sustained-release formulation of the present invention does not preclude a formulation exhibiting a "burst" phenomenon. The controlled or sustained release may be steady state (commonly referred to as "timed release" or zero-order drug release kinetics) such that the drug is released in even amounts over a predetermined time (with or without an initial burst phase), or may be a gradient release.

Controlled or sustained-release formulations are designed to achieve a prolonged therapeutic effect by continuously releasing a medication over an extended period of time after administration of a single dose. A preferred profile in some cases, in controlled or sustained release is zero-order drug release kinetics. Zero-order drug release kinetics can be assessed in in-vitro dissolution models that mimic the stomach or parenteral environment by showing constant release of a drug over a specified period of time.

There are a number of technologies currently available that have been used to provide zero-order drug release kinetics with certain therapeutic agents, such as analgesic and anesthetic drugs (e.g. lidocaine, fentanyl, sufentanil, codeine, hydromorphone, bupivacaine, and trifusal) as well as larger molecules such as cyclodextrin. These include osmotic-based approaches, liposomal systems and bioerodible polymers. Additionally, numerous design concepts have been attempted, and various transport mechanisms including diffusion/dissolution, chemical reactions, osmosis, erosion, and swelling have been explored in connection with identifying delivery systems that exhibit zero-order drug release kinetics. One of the concepts that has demonstrated zero-order drug release kinetics is from hydrophilic swellable matrices with various geometries in connection with morphine, indomethacin and diltiazem HCl, as set forth by Yukinari, et. al, 1993, in "*Swelling controlled zero-order and sigmoidal drug release from thermo-responsive poly(N-isopropylacrylamide-co-butyl methacrylate)hydrogel*" and by Okano, et. al, in 1990, in "*Thermally on-off switching polymers for drug permeation and release*". Drug diffusion from the matrix is accomplished by swelling, dissolution and/or erosion. The major component of these controlled-release systems is a hydrophilic polymer. In general, diffusivity is high in polymers containing amorphous flexible chains and low in crystalline polymers. With changes in morphological characteristics, the mobility of the polymer segments changes and diffusivity can be controlled. Addition of other components, such as a drug, another polymer, soluble or insoluble fillers, or a solvent, can alter the intermolecular forces, free volume, glass transition temperature, and consequently, can alter the transport mechanisms.

U.S. Pat. Nos. 3,997,512, 4,048,256, 4,076,798, 4,095,600, 4,118,470, and 4,122,129, assigned to American Cyanamid Company, describe biocompatible and absorbable polycondensation polyesters, which are the polycondensation product of diglycolic acid and glycols such as ethylene glycol, diethylene glycol, 1,2-propylene glycol, 1,3-propylene glycol, and the like. Specifically, U.S. Pat. No. 4,095,600 describes a reaction product of (a) about 2 to 50% by weight of the polycondensation polyester and (b) polyglycolic acid, based on the total weight of the polycondensation polyester and polyglycolic acid, to form a self-supporting polymeric film for use, for example, in drug delivery. However, these references are silent with respect to the zero-order drug release kinetics exhibited when the polycondensation polyesters are used in combination with a drug.

There also remains a need to have controlled or sustained-release formulations for certain drugs, where zero-order drug release kinetics is desirable.

SUMMARY OF THE INVENTION

Described herein is a formulation comprising a co-polyester comprising (a) the reaction product of a polycondensation polyester and (b) glycolide; wherein the polycondensation polyester comprises the reaction product of diglycolic acid and/or a derivative thereof and ethylene glycol, and the co-polyester comprises about 40% by weight of the polycondensation polyester based on the total weight of the co-polyester; and a drug selected from the group consisting of indomethacin, diclofenac sodium, and ketoprofen.

DETAILED DESCRIPTION

Figure 1:
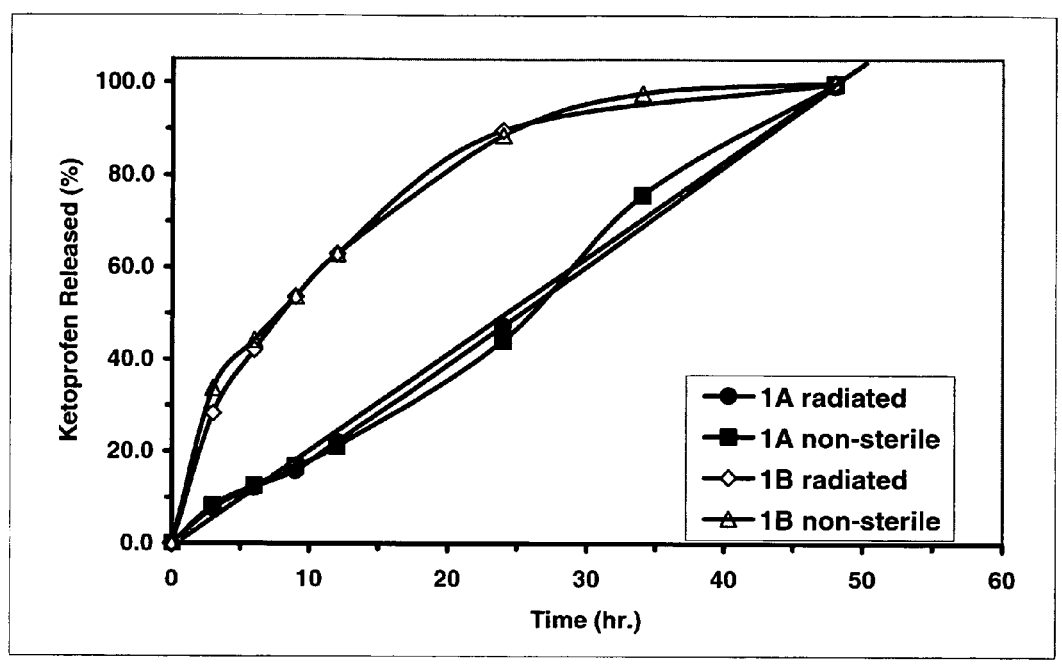
FIG. 1 represents ketoprofen in vitro release profiles for non-sterile films and cobalt sterilized films.

The co-polyester described herein has been found to be effective as a drug delivery carrier in controlled or sustained-release formulations.

In one embodiment, the co-polyester comprises the reaction product of a polycondensation polymer and at least one lactone, wherein the polycondensation polyester comprises the reaction product of diglycolic acid and/or a derivative thereof and ethylene glycol.

The polycondensation polyester may be synthesized by conventional techniques using conventional processes. For example, in a condensation polymerization, diglycolic acid and ethylene glycol may be polymerized in the presence of a catalyst at elevated temperatures and reduced pressures. A variety of catalysts may be used, but organometallic compounds have been found to be useful. The catalyst for the polycondensation step of the synthesis is preferably tin based, e.g., stannous octoate. The most desirable catalyst is dibutyltin oxide and is present in the diglycolic acid/ethylene glycol monomer mixture at a sufficiently effective molar ratio of monomer to catalyst, e.g., ranging from about 5,000/1 to about 100,000/1. For example, the ratio of 10,000/1 has been found to be quite suitable. The reaction is typically carried out at a temperature range from about 100° C. to about 220° C., preferably from about 140° C. to about 180° C., under an inert atmosphere until esterification of diglycolic acid is complete. Preferably, 165° C. has been found to be a desirable reaction temperature when employing a vertically stirred reactor. It should be noted that the optimum reaction temperature may be reactor and catalyst level dependent but can be found by one having only ordinary skill through the use of experiments. The first stage of the polycondensation reaction (inert gas at atmospheric pressure) is followed by polymerization under reduced pressure until the desired molecular weight and viscosity are achieved.

The weight average molecular weight of the polycondensation polymer can range generally from about 2,000 to about 50,000 g/mol, preferably from about 7,000 to about 20,000 g/mol, most preferably about 10,000 g/mol. This corresponds to an inherent viscosity range from about 0.25 to about 0.60 dL/g.

When the molecular weight of the polycondensation polymer is lower than about 2,000 g/mol, the molecular weight of the final co-polyester is too low to achieve the desired mechanical properties necessary for many medical device applications. Although molecular weight can be increased with increasing reaction time, it becomes increasingly difficult to achieve very high molecular weight. We have found, in general, that a molecular weight of the polycondensation polymer greater than about 50,000 g/mol, is not necessary to achieve desirable properties. One could however envision that this value is not an absolute bar. One might for instance, increase the molecular weight of the polycondensation polymer, and lower the amount of the lactone component used in the preparation of the final co-polyester.

The amount of polycondensation polyester used to prepare the co-polyester is about 40 to 50% by weight based on the total weight of the co-polyester.

Suitable lactone monomers include, but are not limited to, glycolide, lactide (l, d, dl, meso), p-dioxanone, trimethylene carbonate, epsilon-caprolactone, delta-valerolactone, beta-butyrolactone, epsilon-decalactone, 2,5-diketomorpholine, pivalolactone, alpha,alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations of two or more thereof. The preferred lactone monomer includes glycolide.

In one embodiment, the co-polyester may comprise the reaction product of a polycondensation polyester and a lactone such as glycolide.

In another embodiment, the co-polyester may comprise the reaction product of a polycondensation polyester and two or more lactones. For example, the co-polyester may comprise the reaction product of the polycondensation polyester, at least 75 mole percent glycolide based on the total moles of lactone, and a second lactone monomer.

The co-polyesters of the present invention may be conveniently synthesized by reaction of a dihydroxy poly(alkylene diglycolate) homopolymer or copolymer with a lactone by conventional techniques using conventional processes. For example, the polycondensation polyester is used as an $\alpha,\omega$-dihydroxy macroinitiator in a subsequent ring opening polymerization (ROP) with a lactone or a lactone mixture. The lactone monomers are copolymerized into the polycondensation polyester in the presence of a conventional organometallic catalyst at elevated temperatures. The catalyst for the ROP may be already present as residual catalyst in the polycondensation polyester or may be additional catalyst added in this second step of the synthesis. A suitable catalyst added at the time of the ROP can be an organometallic catalyst. The ring-opening organometallic catalyst is preferably tin based, e.g., stannous octoate, and is present in a sufficiently effective amount in the monomer mixture, preferably at a molar ratio of lactone monomer-to-catalyst ranging from about 20,000/1 to infinity (i.e. no additional catalyst used). Thus one might utilize a tin-IV compound such as dibutyltin oxide at a diacid, for instance, diglycolic acid-to-catalyst ratio of about 10,000/1 to prepare the polycondensation polyester and then add a tin-II compound such as stannous octoate at a lactone-to-added-catalyst molar ratio of about 240,000/1 at the time of the ring opening polymerization. The co-polyesters of the present invention may be synthesized alternately with no additional catalyst being added at the time of the ROP as described in Example 3A.

The ROP step can be immediately conducted in the same reactor as that used to synthesize the polycondensation polyester immediately after the completion of the polycondensation step, if the reactor can provide adequate heat transfer and agitation. The lactone or lactone mixture can be added as a solid, a slurry, or in molten form. Alternately, the ROP can be conducted in a separate reactor at a later date, or in the reactor used for the polycondensation polyester at a later date. If this is the case, the polycondensation polyester is discharged from its reactor and is stored in an environment that minimizes water pick up and hydrolysis. In the case of adding glycolide monomer, the monomer can be added as a solid. The reactor is closed and the pressure reduced. The reactor is usually held under vacuum for a prolonged period of time, for instance overnight, to allow drying. Nitrogen is then introduced into the reactor to bring the pressure to slightly greater than one atmosphere, and the purge cycle repeated for a total of three times. The temperature of the reaction mass is brought up to 130° C. Once at this temperature, the agitator is activated. The temperature is then increased to 150° C. to complete the mixing. This mixing step is essential to produce the co-polyesters of the present invention as inadequate mixing tends to allow the formation of homopolymeric sequences which can then crystallize to an extent greater than optimum. To ensure that reactants are fully mixed, in-situ spectroscopic probes (such as Near-Infrared) can be conveniently used. If additional catalyst is to be added, it is typically added once the batch has been completely mixed. The temperature is quickly brought up to the final reaction temperature, with 210° C. being a most preferred temperature, and held there for typically 2 hours. The exact reaction conditions will depend on the catalyst and its level; final reaction temperatures can vary from about 195° C. to 235° C., and more preferably from about 200° C. to about 220° C. Reaction times can vary from about 30 minutes to a few hours, depending on the catalyst and it level, and is typically conducted until the desired conversion of monomer to polymer is achieved.

An alternate reaction scheme that has been employed to prepare the co-polyesters of the invention has involved adding the lactone as a molten stream into the reactor. Thus the polycondensation polyester is added first, typically as a molten stream and the reactor evacuated. The reactor is heated to 130° C. Molten glycolide (or other glycolide rich mixture) at a temperature of 100° C. is added to the reactor. Although the batch temperature drops slightly, it is quickly brought back up to 130° C. at which point mixing is started. At this point, the process that was described above is followed.

Under the above described conditions, the co-polyesters of polycondensation polyester and lactones, will typically have a weight average molecular weight of about 10,000 g/mol (a.k.a. Daltons) to about 100,000 g/mol, preferably about 15,000 g/mol to about 50,000 g/mol, and more preferably about 20,000 g/mol to about 40,000 g/mol, most preferably about 30,000 g/mol. These molecular weights are sufficient to provide an effective inherent viscosity, typically between about 0.30 to about 2.0 deciliters per gram (dL/g), preferably about 0.40 to about 1.0 dL/g, more preferably about 0.50 to about 0.8 dL/g and most preferably about 0.65 dL/g, as measured in a 0.1 g/dL solution of hexafluoroisopropanol (HFIP) at 25° C.

As shown in the Examples below, a co-polyester has been developed that is capable of providing nearly constant delivery of the following drugs during the time of their evaluation in vitro: Indomethacin, diclofenac sodium, and ketoprofen. Although only three compounds that were tested, the co-polyester may prove useful as a drug carrier for other drug entities. It is likely that the erosion characteristics of the copolymer that was tested in these preparations in combination with the drug loading within the matrix of the copolymer polymer was able to control the release of each of these medications in the in vitro environment where they were tested. It is noted that geometry plays a significant role in the release profiles. Examples of the geometry of the drug carrier include but not limited to films, discs, rods or microspheres. In particular, when the geometry is a film, the thickness of the film is important. The range of the thickness is from a range such that it is sufficient to provide controlled release while avoiding excess amount of polymers used.

In particular, the co-polyester is capable of providing nearly constant release characteristics, for each of the drugs, for extended periods of time ranging from 48 to 200 hours. In particular, the drug loading that is effective ranges from 0.5% by weight to about 20% by weight based on the total weight of the co-polyester, preferably ranges from 1% by weight to about 15% by weight based on the total weight of the co-polyester, more preferably from 2% by weight to about 10% by weight based on the total weight of the co-polyester. The daily therapeutic range for the above-mentioned drugs for a 60 Kg adult are: 5 mg~200 mg for indomethacin, 5 mg~200 mg for diclofenac sodium and 10 mg~300 mg for ketoprofen.

Example 1

Sample 1A, a copolymer comprising (1) 40% by weight of a polycondensation polymer made by reacting diglycolic acid and ethylene glycol, based on the total weight of copolymer, and (2) a glycolide polyester; and Sample 1B, a copolymer comprising (1) 20% by weight of a polycondensation polymer made by reacting diglycolic acid and ethylene glycol, based on the total weight of copolymer, and (2) a 80/20 glycolide/caprolactone polyester; were individually dry blended with 15% ketoprofen and later compounded using a lab-scale compounder manufactured by Daca. After compounding, extruded samples were cut into small pieces, from which several 5-mil films were compression molded using a compression molder available from Tetrahedron. Some of the film samples were sterilized by γ irradiation using a cobalt source. The radiation exposure was 25 kGy. In-vitro drug release testing was conducted in a shaker water bath maintained at 37° C. and agitated at 30 cpm. Polymer films (1 cm×1 cm) loaded with ketoprofen were placed in 20 mL glass scintillation vials filled with 20 mLs of 0.1 M phosphate buffer solution (pH 7.4) and sealed with a screw cap. The scintillation vials were placed in a shaker water bath maintained at 37° C. and agitated at 30 cpm. Buffer solution aliquots were collected at designated time intervals (3, 6, 9, 12, 24, 36, 48 and 72 hours); during these time periods, the buffer in each vial was replaced with fresh media. The ketoprofen contents were measured using a HPLC method.

HPLC assay for ketoprofen follows. The mobile phase is prepared by mixing HPLC grade acetonitrile and 0.04 M $KH_2PO_4$, pH3.5 buffer, filtered through 0.45μ filter in 40:60 ratio. The standard solutions was prepared by dissolving about 50 mg of ketoprofen reference standard in approximately 40.0 mL of mobile phase, using sonication if necessary, in a 50 mL volumetric flask. Bring to volume with mobile phase and dilute the standard stock solution with mobile phase to desired concentrations. The HPLC conditions are:

Column: Phenomenex Luna Pheny-Hexyl, 50 mm×4.6 mm, 3μ

Mobile phase: 40:60 acetonitrile: 0.04 M $KH_2PO_4$, pH3.5 buffer

Flow rate: 0.75 mL/min

Detection: UV 233 nm

Injection Volume: 5 μL

Run Time: 5 min

The data generated is summarized in FIG. 1. It should be noted that non-sterile and sterile films of Sample 1A provided nearly constant release of ketoprofen up to about 48 hours. The heavy bold line in FIG. 1 is an idealized representation of controlled release, specifically zero-order release over that range. FIG. 1 represents ketoprofen in vitro release profiles for non-sterile films and cobalt sterilized films, where the ketoprofen was normalized to the target drug loading, i.e.

15%. Note that Sample 1A=inventive and 1B=comparative; and radiation has no effect on the release profile.

Example 2

In separate experiments, Sample 2A, a copolymer comprising (1) 40% by weight of a polycondensation polymer made by reacting diglycolic acid and ethylene glycol, based on the total weight of copolymer, and (2) a glycolide polyester; Sample 2B, a copolymer comprising (1) 20% by weight of a polycondensation polymer made by reacting diglycolic acid and ethylene glycol, based on the total weight of copolymer, and (2) a 80/20 glycolide/caprolactone polyester; Sample 2C, a copolymer comprising (1) 50% by weight of a polycondensation polymer made by reacting diglycolic acid and ethylene glycol, based on the total weight of copolymer, and (2) a glycolide polyester, having an IV=0.81; Sample 2D, a copolymer comprising (1) 50% by weight of a polycondensation polymer made by reacting diglycolic acid and ethylene glycol, based on the total weight of copolymer, and (2) a glycolide polyester, having an IV=0.53; Sample 2E, a copolymer comprising (1) 40% by weight of a polycondensation polymer made by reacting diglycolic acid and ethylene glycol, based on the total weight of copolymer, and (2) a lactide polyester, Sample 2F, a copolymer comprising (1) 50% by weight of a polycondensation polymer made by reacting diglycolic acid and ethylene glycol, based on the total weight of copolymer, and (2) a lactide polyester; were each individually dry blended with 15% ketoprofen and later compounded using a lab-scale compounder manufactured by Daca. After compounding, extruded samples were cut into small pieces, from which several 5-mil films were compression molded using a compression molder available from Tetrahedron. Polymer films (1 cm×1 cm) loaded with ketoprofen were placed in 20 mL glass scintillation vials filled with 20 mLs of 0.1 M phosphate buffer solution (pH 7.4) and sealed with a screw cap. The scintillation vials were placed in a shaker water bath maintained at 37° C. and agitated 30 cpm. Buffer solution aliquots were collected at designated time intervals (3, 6, 9, 12, 24, 36, 48 and 72 hours). During these time periods, the buffer in each vial was replaced with fresh media. The ketoprofen concentrations were measured using a HPLC method.

HPLC assay for ketoprofen follows. The mobile phase is prepared by mixing HPLC grade acetonitrile and 0.04 M $KH_2PO_4$, pH3.5 buffer, filter through 0.45μ filter in 40:60 ratio. The standard solutions was prepared by dissolving about 50 mg of ketoprofen reference standard in approximately 40.0 mL of mobile phase, using sonication if necessary, in a 50 mL volumetric flask. Bring to volume with mobile phase and dilute the standard stock solution with mobile phase to desired concentrations. The HPLC conditions are the same as in Example 1.

Figure 2:
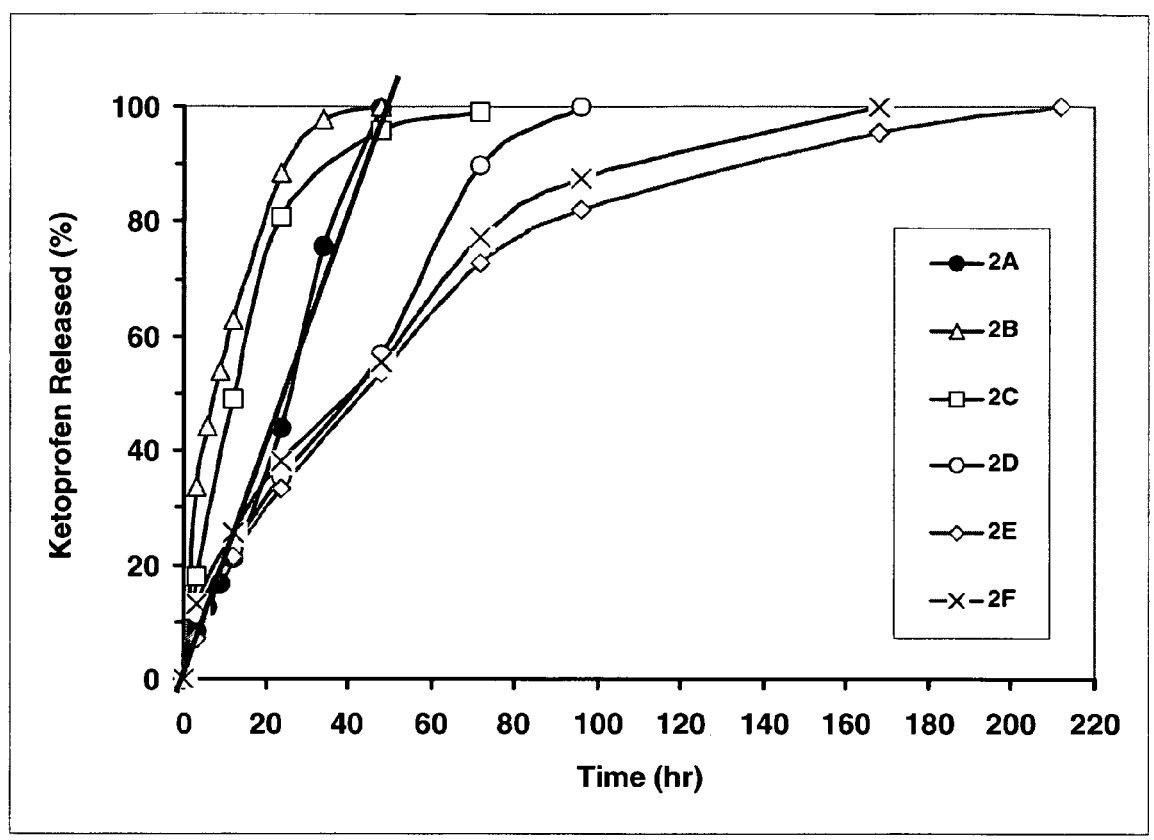
FIG. 2 represents ketoprofen in vitro release profiles for non-sterile films.

The data generated is summarized in FIG. 2. It should be noted that non-sterile and sterile films of Sample 2A provided nearly constant release up to about 48 hours. The heavy bold lines in FIG. 2 represents an idealized constant release rate. FIG. 2 represents ketoprofen in vitro release profiles for non-sterile films, where ketoprofen was normalized to the target drug loading, i.e. 15%. Note that Sample 2A=inventive and 2B-2F=comparative.

Example 3

In separate experiments, Samples 3A and 3B, each a copolymer comprising (1) 40% by weight of a polycondensation polymer made by reacting diglycolic acid and ethylene glycol, based on the total weight of copolymer, and (2) a glycolide polyester, was individually dry blended with 15% diclofenac sodium salt (3A) and 15% diclofenac free acid (3B), respectively, and later compounded using a lab-scale compounder manufactured by Daca. After compounding, extruded samples were cut into small pieces, from which several 5-mil films were compression molded using a compression molder available from Tetrahedron. Polymer films (1 cm×1 cm) loaded with the appropriate active agent were placed in 20 ml glass scintillation vials filled with 20 mls of 0.01 M phosphate buffer solution (pH 7.4) and sealed with a screw cap. The scintillation vials were placed in a shaker water bath maintained at 37° C. and agitated 30 cpm. Buffer solution aliquots were collected at designated time intervals (3, 6, 9, 12, 24, 36, 48 and 72 hours); during these time periods, the buffer in each vial was replaced with fresh media. The amounts of active agent (diclofenac sodium or diclofenac) released into the buffer solution were measured using a HPLC method.

HPLC assay for diclofenac sodium salt follows. First make phosphate buffer, pH 2.5 by mixing equal volume of 0.01 M phosphoric acid and 0.01 M monobasic sodium phosphate and adjust pH to 2.5 with additional portions of the appropriate component.

Figure 3:
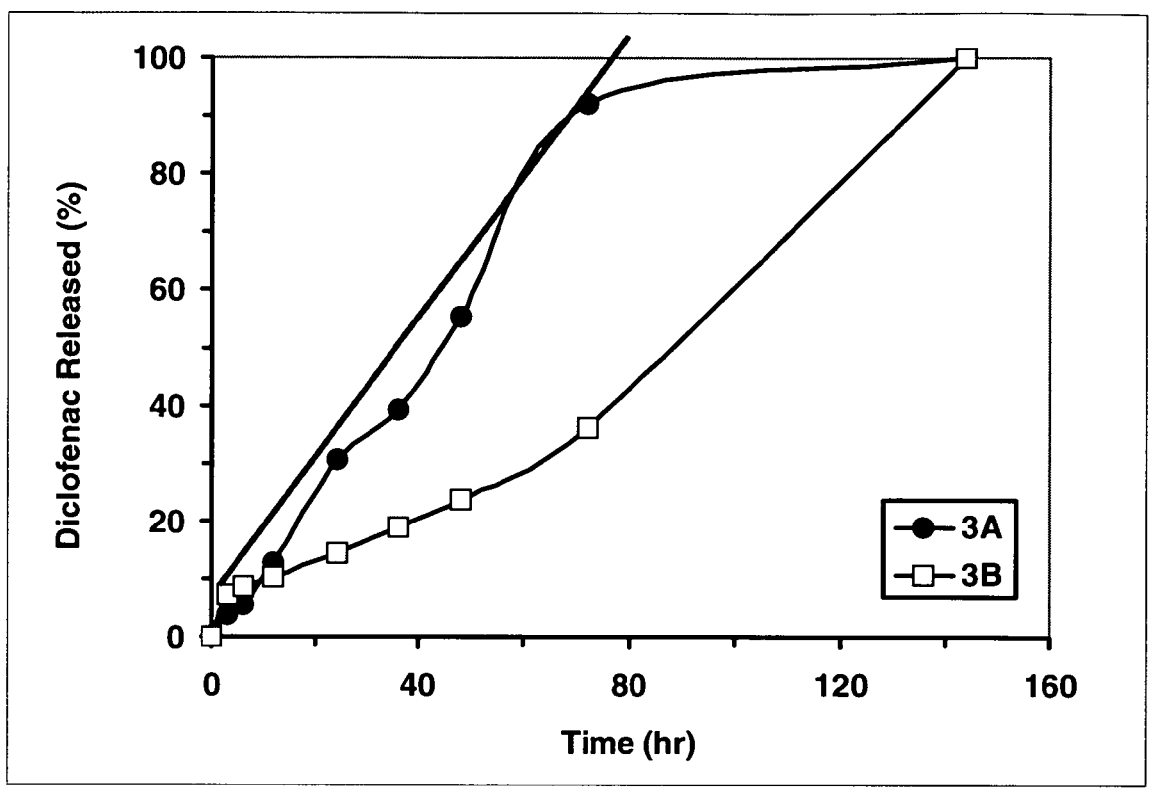
FIG. 3 represents diclofenac sodium and diclofenac free acid in vitro release profiles.

The mobile phase is prepared by mixing methanol and pH 2.5 phosphate buffer in ratio of 70:30. The standard solutions was prepared by dissolving about 50 mg of diclofenac sodium reference standard in approximately 40.0 mL of MeOH, using sonication if necessary, in a 50 mL volumetric flask. Bring to volume with methanol. Then dilute the standard stock solution with diluent (70:30 MeOH:water) to desired concentrations. The HPLC conditions are:

Column: Phenomenex Luna C18,150 mm×4.6 mm, 5μ
Mobile phase: MeOH: phosphate buffer 70:30
Flow rate: 1 mL/min
Detection: UV 254 nm
Injection Volume: 10 μL
Run Time: 15 min The data generated is summarized in FIG. 3. It should be noted that films of Sample 3A loaded with the sodium salt of diclofenac provided controlled release of diclofenac sodium up to about 72 hours with a release profile approximating constant release of the drug over that time period. The heavy bold lines in FIG. 3 represents an idealized constant release rate. FIG. 3 represents diclofenac sodium and diclofenac free acid in vitro release profiles, where the diclofenac sodium and diclofenac free acid was normalized to their total drug contents. Note that Sample 3A=inventive and 3B=comparative.

Example 4

In separate experiments, a copolymer comprising (1) 40% by weight of a polycondensation polymer made by reacting diglycolic acid and ethylene glycol, based on the total weight of copolymer, and (2) a glycolide polyester, was individually dry blended with 15% indomethacin and the dry blends later compounded using a lab-scale compounder manufactured by Daca. After compounding, extruded samples were cut into small pieces, from which several 10-mil (Samples 4A), 7-mil (Sample 4B), and 5-mil (Sample 4C) films were compression molded using a compression molder available from Tetrahedron. Some of the film samples were sterilized by γ-irradiation using a cobalt source. The radiation exposure was 25 kGy. Polymer films (1 cm×1 cm) loaded with ketoprofen were placed in 20 mL glass scintillation vials filled with 20 mL of 0.1 M phosphate buffer solution (pH 7.4) and sealed with a screw cap. The drug release testing was conducted in a shaker water bath maintained at 37° C. and agitated 30 cpm. Buffer solution aliquots were collected at designated time intervals (3, 6, 9, 12, 24, 36, 48 and 72 hours); during these time periods, the buffer in each vial was replaced with fresh media. The indomethacin contents were measured using a HPLC method.

HPLC assay for indomethacin is following. The first mobile phases were prepared. Mix equal volume of phosphate buffer (0.01 M dibasic sodium phosphate and 0.01 M monobasic sodium phosphate) and acetonitrile. The second mobile phase is water. The standard solutions is prepared by dissolving about 50 mg of indomethacin reference standard in 40.0 mL of methanol, using sonication if necessary, in a 50 mL volumetric flask. Bring the standard solution to volume with methanol and dilute the standard stock solution with methanol to desire concentrations. The HPLC conditions are:

Column: Phenomenex Luna C18, 25 cm×4.6 mm, 5μ (For dissolution test, use 15 cm or 10 cm column)
Mobile phase: A: B 80:20
Flow rate: 1 mL/min
Detection: UV 254 nm
Injection Volume: 10 μL
Run Time: 10 min (5 min for short column)

Figure 4:
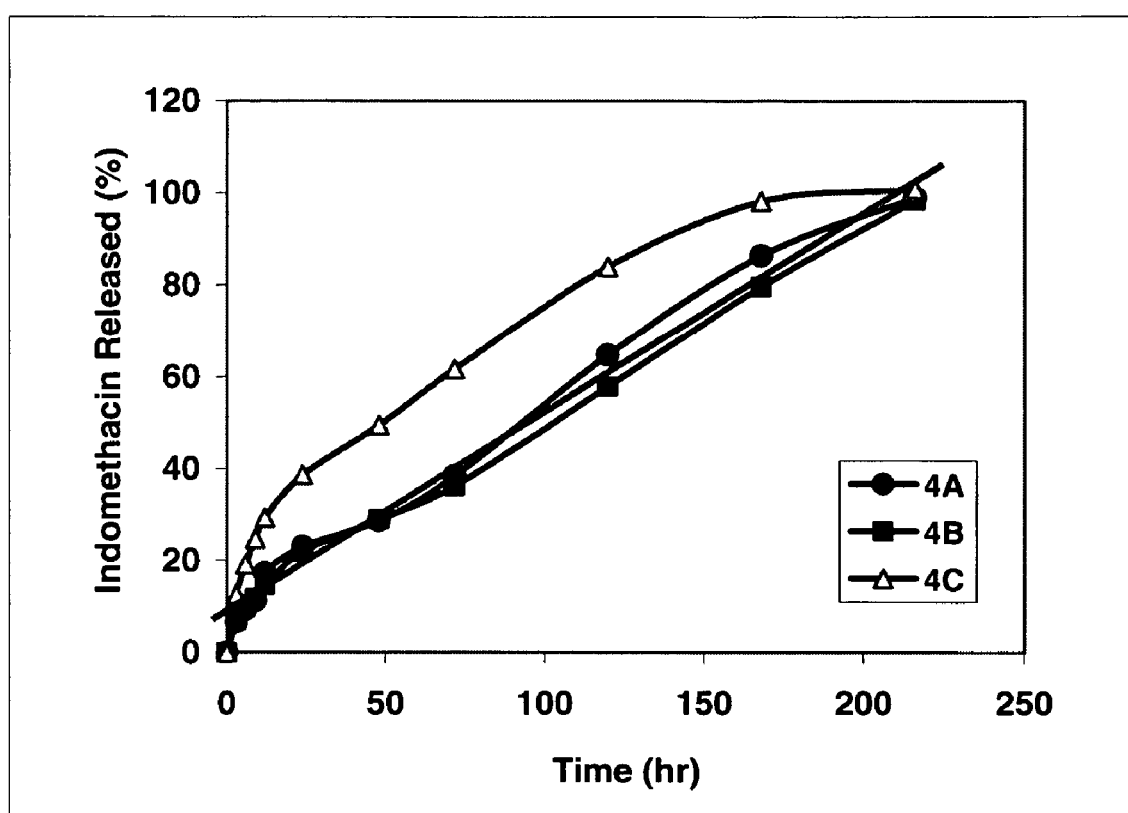
FIG. 4 represents the release profile of Indomethacin released from radiated 10 mil, 7 mil and 5 mil thick films.

All the samples exhibited controlled release longer than 200 hrs or over 8 days. The results show that nearly constant release of indomethacin is achieved for 200 hours from radiated indomethacin loaded 10 mil thick and 7 mil thick, Samples 4A, and 4B. The heavy bold lines in FIG. 4 represents an idealized constant release rate. FIG. 4 represents the release profile of Indomethacin released from radiated 10 mil, 7 mil and 5 mil thick films, where the amounts of in vitro drug released were normalized with its total drug content. Note that Samples 4A-4C were loaded with 15% of indomethacin; and that Sample 4A and 4B=inventive; and 4C=comparative).

Example 5

In separate experiments, Sample 5A, a copolymer comprising (1) 40% by weight of a polycondensation polymer made by reacting diglycolic acid and ethylene glycol, based on the total weight of copolymer, and (2) a glycolide polyester; Sample 5B, a copolymer comprising (1) 40% by weight a polycondensation polymer made by reacting 3,6 dioxaoctanedioic acid, diglycolic acid and ethylene glycol, where the molar ratio of diacids in the mixture is 75% 3,6 dioxaoctanedioic acid and 25% diglycolic acid. and (2) a glycolide polyester; and Sample 5C, a copolymer comprising (1) 20% by weight of a polycondensation polymer made by reacting diglycolic acid and ethylene glycol, based on the total weight of copolymer, and (2) a 80/20 glycolide/caprolactone polyester; w were individually dry blended with 15% indomethacin and later compounded using a lab-scale compounder manufactured by Daca. After compounding, extruded samples were cut into small pieces, from which several 5-mil films were compression molded using a compression molder available from Tetrahedron. Some of the film samples were sterilized by γ-irradiation using a using cobalt source. The radiation exposure was 25 kGy. Polymer films (1 cm×1 cm) loaded with ketoprofen were placed in 20 mL glass scintillation vials filled with 20 mLs of 0.1 M phosphate buffer solution (pH 7.4) and sealed with a screw cap. The scintillation vials were placed in a shaker water bath maintained at 37° C. and agitated 30 cpm (circle per minute). Buffer solution aliquots were collected at designated time intervals (1, 3, 6, 12, 24, 36, 48 and 72 hours); during these time periods, the buffer in each vial was replaced with fresh media. The indomethacin contents were measured using a HPLC method.

HPLC assay for indomethacin is following. The first mobile phases were prepared. Mix equal volume of phosphate buffer (0.01 M dibasic sodium phosphate and 0.01 M monobasic sodium phosphate) and acetonitrile. The second mobile phase is water. The standard solutions is prepared by dissolving about 50 mg of indomethacin reference standard in 40.0 mL of methanol, using sonication if necessary, in a 50 mL volumetric flask. Bring the standard solution to volume with methanol and dilute the standard stock solution with methanol to desire concentrations. The HPLC conditions are the same as in Example 4.

Figure 5:
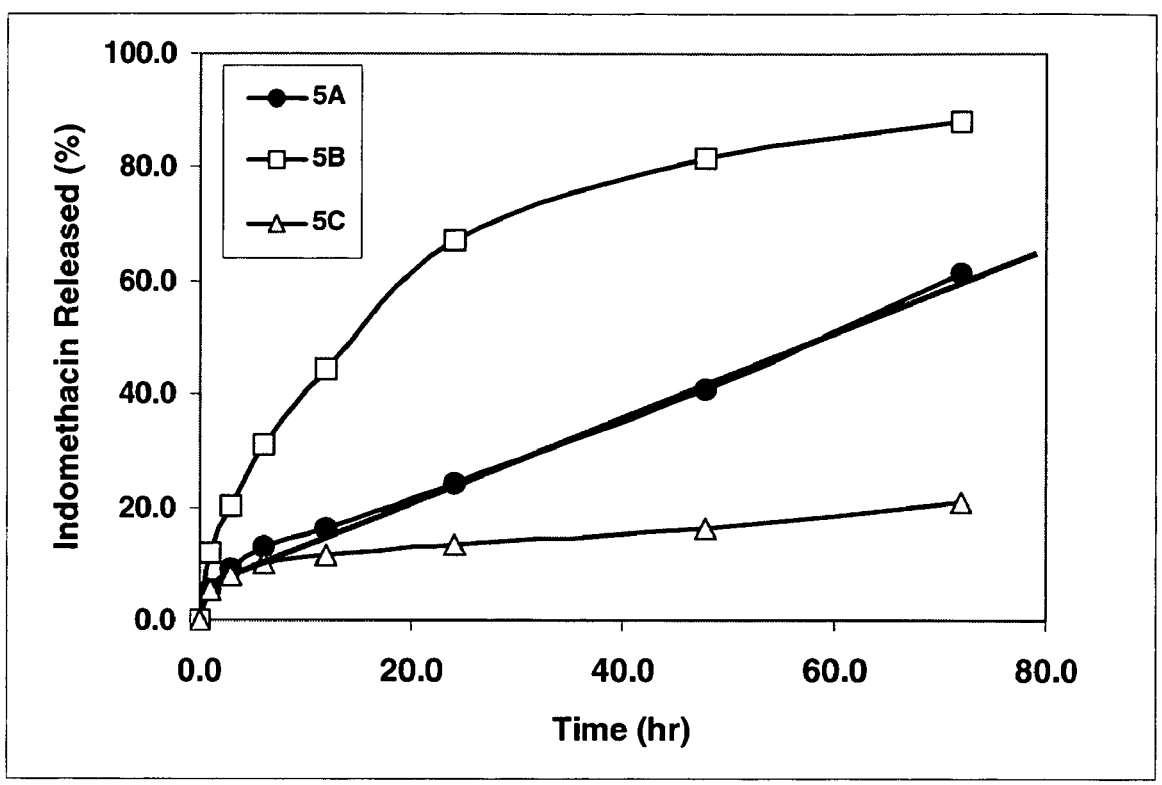
FIG. 5 represents the release profile of Indomethacin released from Samples 5A-5C.

The data generated for polymers films in buffer solutions with pH of 7.4 is summarized in FIG. 5. Indomethacin release profiles differ significantly among these three samples. It is also noticed that indomethacin release profile from Sample 5A approximates constant release. The heavy bold lines in FIG. 5 represents an idealized constant release rate. FIG. 5 represents the release profile of Indomethacin released from Samples 5A-5C, where the amounts of in vitro drug released were normalized with its total drug content. Note that Sample 5A=inventive; and 5B and 5C=comparative)

What is claimed is:

1. A formulation comprising:
   (a) a co-polyester comprising the reaction product of a polycondensation polyester and glycolide,
   wherein the polycondensation polyester comprises the reaction product of diglycolic acid and/or a derivative thereof and ethylene glycol; and
   the co-polyester comprises about 40% by weight of the polycondensation polyester based on the total weight of the co-polyester; and
   (b) a drug selected from the group consisting of indomethacin, diclofenac sodium, and ketoprofen.

2. A formulation of claim 1 wherein the drug is released via a controlled or sustained release profile.

3. A formulation of claim 1 wherein the drug is released via a zero-order drug release kinetics.

4. A formulation of claim 2 wherein the controlled or sustained release profile is a zero-order drug release kinetics.

5. A formulation of claim 1 wherein the range of the drug is from 0.5% by weight to about 20% by weight based on the total weight of the co-polyester.

6. A formulation of claim 1 wherein the range of the drug is from 1% by weight to about 15% by weight based on the total weight of the co-polyester.

7. A formulation of claim 1 wherein the range of the drug is from 2% by weight to about 10% by weight based on the total weight of the co-polyester.

* * * * *